United States Patent
Kamo et al.

(10) Patent No.: US 11,543,647 B2
(45) Date of Patent: Jan. 3, 2023

(54) OBJECTIVE OPTICAL SYSTEM FOR ENDOSCOPE, ENDOSCOPE, AND IMAGE PICKUP UNIT

(71) Applicant: OLYMPUS CORPORATION, Hachioji (JP)

(72) Inventors: Yuji Kamo, Hino (JP); Yoshifumi Tsuji, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 466 days.

(21) Appl. No.: 16/680,452

(22) Filed: Nov. 11, 2019

(65) Prior Publication Data

US 2020/0081240 A1    Mar. 12, 2020

Related U.S. Application Data

(63) Continuation of application No. PCT/JP2018/009237, filed on Mar. 9, 2018.

(30) Foreign Application Priority Data

Jun. 22, 2017   (JP) .............................. JP2017-122540

(51) Int. Cl.
*G02B 23/24* (2006.01)
*G02B 23/26* (2006.01)
*G02B 9/62* (2006.01)

(52) U.S. Cl.
CPC ............ *G02B 23/243* (2013.01); *G02B 9/62* (2013.01); *G02B 23/2446* (2013.01); *G02B 23/26* (2013.01)

(58) Field of Classification Search
CPC .. G02B 9/62; G02B 13/0045; G02B 15/1465; G02B 23/24–2492
See application file for complete search history.

(56) References Cited

U.S. PATENT DOCUMENTS 4,867,546 A * 9/1989 Nishioka ................ G02B 13/06
                                                                 359/714
5,050,974 A   9/1991 Takasugi et al.
(Continued)

FOREIGN PATENT DOCUMENTS

CN   105899993 A   8/2016
CN   109073864 A   12/2018
(Continued)

OTHER PUBLICATIONS

International Search Report (ISR) dated May 22, 2018 (and English translation thereof) issued in International Application No. PCT/JP2018/009237.

(Continued)

*Primary Examiner* — Nicholas R. Pasko
(74) *Attorney, Agent, or Firm* — Holtz, Holtz & Volek PC

(57) ABSTRACT

An objective optical system for endoscope includes a first lens having a negative refractive power, a second lens having a positive refractive power, an aperture stop, a third lens having a positive refractive power, a fourth lens having a positive refractive power, a fifth lens having a negative refractive power, and a sixth lens having a positive refractive power. The second lens is a meniscus lens having a convex surface directed toward an image side and the third lens is a meniscus lens having a convex surface directed toward the image side. A cemented lens having a positive refractive power is formed by the fourth lens and the fifth lens. The sixth lens is cemented to an image sensor, and the following conditional expression (1''') is satisfied:

$$1 \le (r3f + r3r)/(r3f - r3r) \le 5 \qquad (1''').$$

12 Claims, 5 Drawing Sheets

(56) References Cited

U.S. PATENT DOCUMENTS

| | | | |
|---|---|---|---|
| 5,547,457 A | 8/1996 | Tsuyuki et al. | |
| 5,999,337 A * | 12/1999 | Ozaki | G02B 9/10 359/740 |
| 6,537,208 B1 | 3/2003 | Konno | |
| 8,441,529 B2 | 5/2013 | Sasamoto | |
| 8,724,230 B2 | 5/2014 | Morita | |
| 9,568,725 B2 | 2/2017 | Ushio | |
| 10,018,827 B2 | 7/2018 | Ushio | |
| 10,809,521 B2 * | 10/2020 | Tsuji | G02B 23/243 |
| 2012/0147164 A1 | 6/2012 | Sasamoto | |
| 2013/0163092 A1 | 6/2013 | Morita | |
| 2015/0207998 A1 * | 7/2015 | Lin | H04N 5/23296 359/713 |
| 2016/0306162 A1 * | 10/2016 | Ushio | G02B 9/62 |
| 2017/0343790 A1 | 11/2017 | Ushio | |
| 2018/0210177 A1 * | 7/2018 | Liu | G02B 13/0045 |
| 2018/0231749 A1 * | 8/2018 | Namii | G02B 23/2415 |
| 2019/0064500 A1 | 2/2019 | Tsuji | |
| 2019/0064599 A1 | 2/2019 | Zhao et al. | |

FOREIGN PATENT DOCUMENTS

| | | | |
|---|---|---|---|
| JP | H0274912 A | 3/1990 | |
| JP | H06222263 A | 8/1994 | |
| JP | 2596810 B2 | 4/1997 | |
| JP | 2001083400 A | 3/2001 | |
| JP | 3723637 B2 | 9/2005 | |
| JP | 5927368 B1 | 6/2016 | |
| WO | 2011145505 A1 | 11/2011 | |
| WO | 2013002019 A1 | 1/2013 | |
| WO | 2016031586 A1 | 3/2016 | |
| WO | WO-2016031586 A1 * | 3/2016 | A61B 1/00188 |
| WO | 2016204001 A1 | 12/2016 | |
| WO | 2018042797 A1 | 3/2018 | |

OTHER PUBLICATIONS

Japanese Office Action dated Aug. 15, 2018 (and English translation thereof) issued in counterpart Japanese Patent Application No. JP 2018-537883.

Written Opinion of the International Searching Authority dated May 22, 2018 issued in International Application No. PCT/JP2018/009237.

Chinese Office Action (and English language translation thereof) dated Nov. 3, 2021, issued in counterpart Chinese Application No. 201880033237.6.

International Preliminary Report on Patentability (IPRP) (and English language translation thereof) dated Jan. 2, 2020 issued in counterpart International Application No. PCT/JP2018/009237.

* cited by examiner

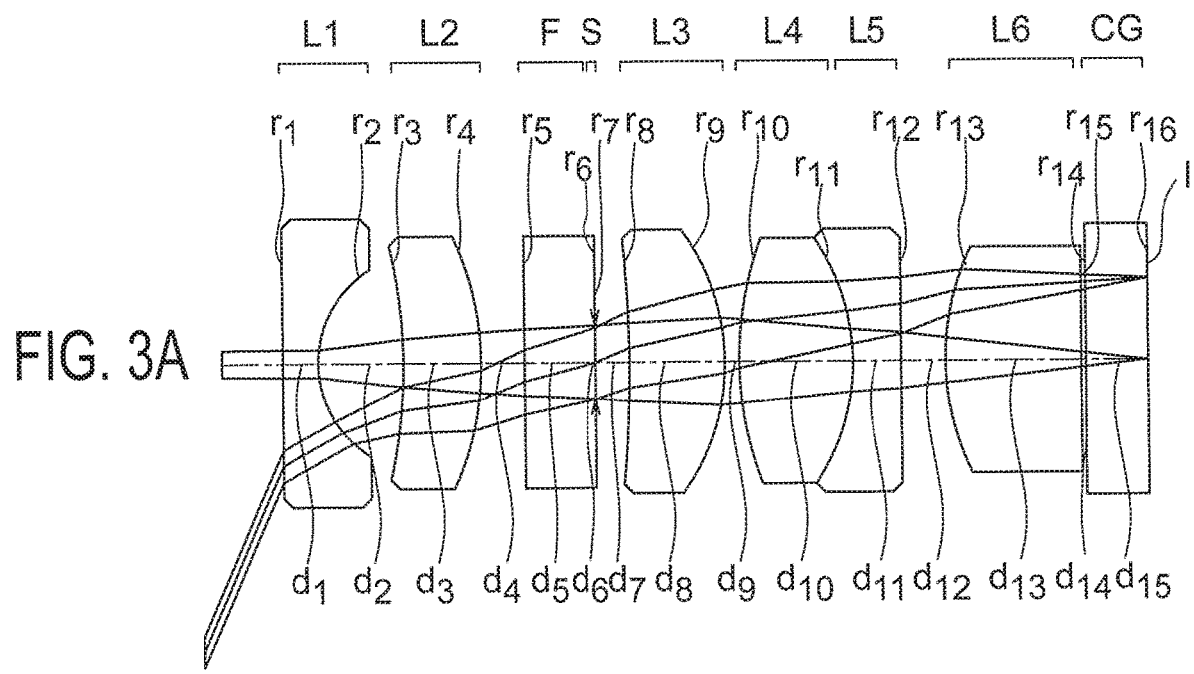
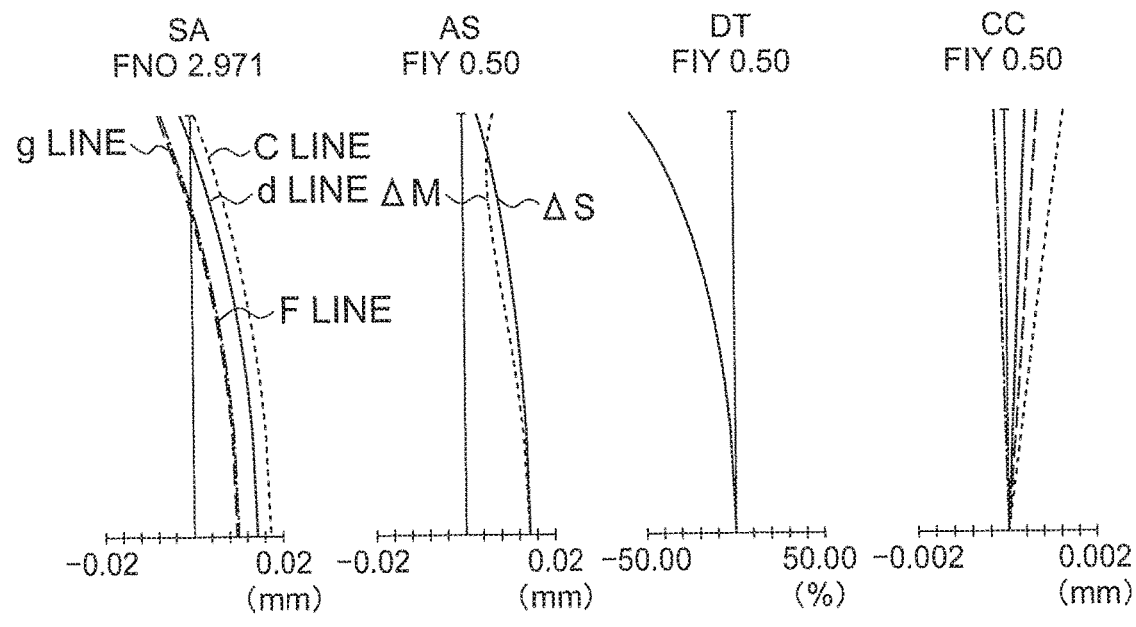

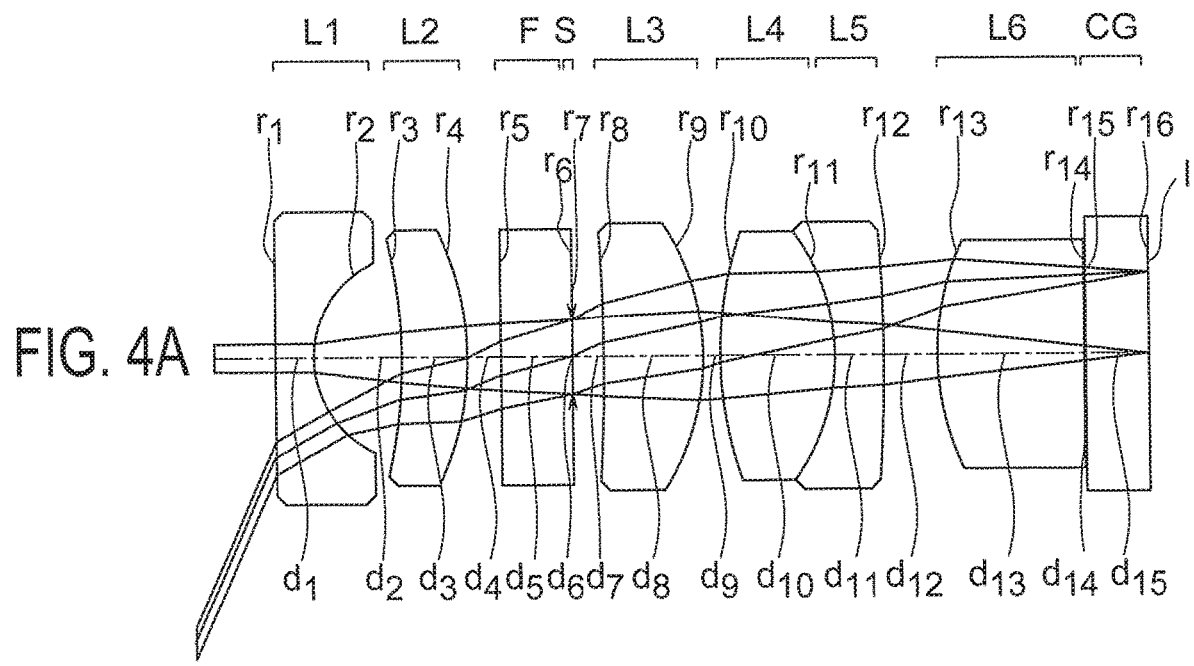
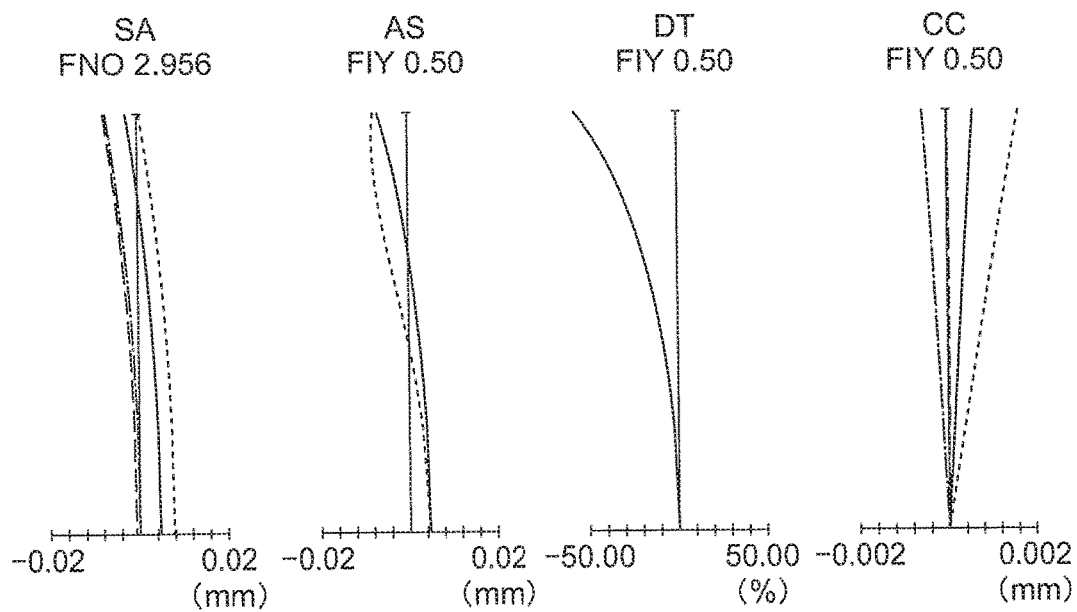

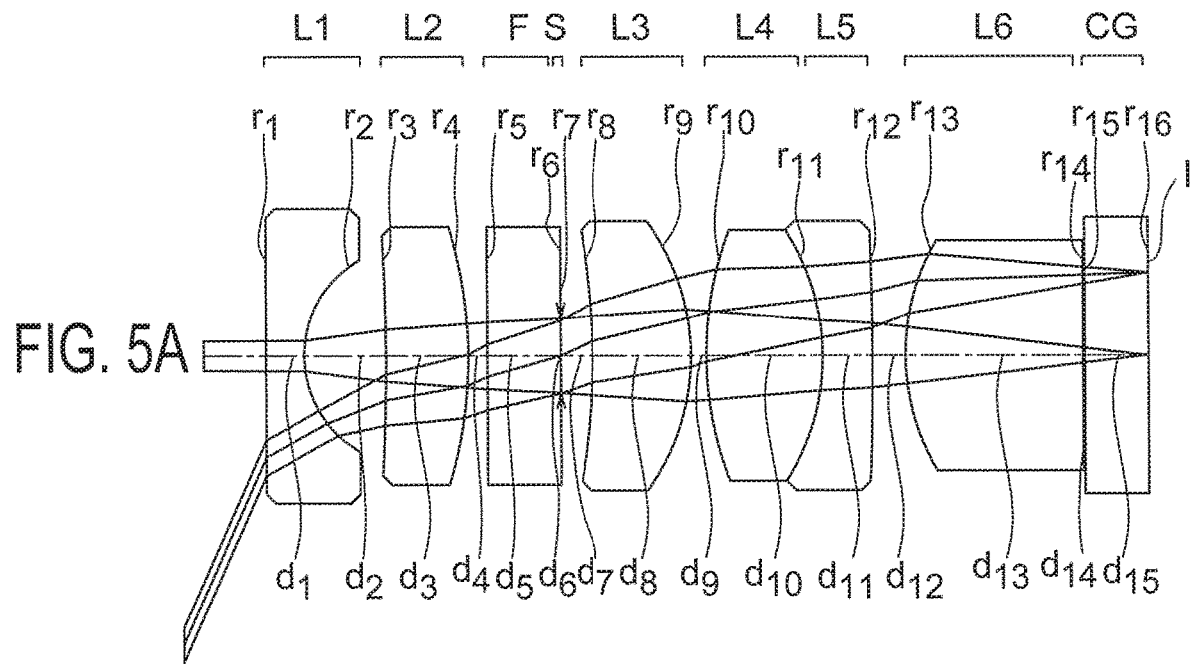
FIG. 5A
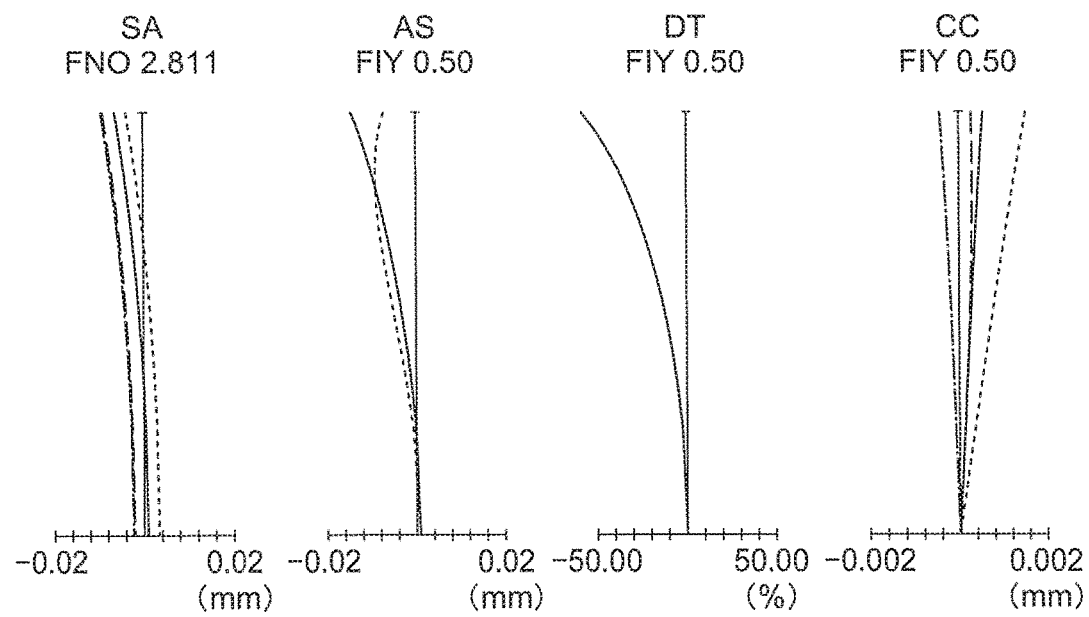
FIG. 5B
SA
FNO 2.811
FIG. 5C
AS
FIY 0.50
FIG. 5D
DT
FIY 0.50
FIG. 5E
CC
FIY 0.50

OBJECTIVE OPTICAL SYSTEM FOR ENDOSCOPE, ENDOSCOPE, AND IMAGE PICKUP UNIT

CROSS-REFERENCE TO RELATED APPLICATION

The present application is a continuation application of PCT/JP2018/009237 filed on Mar. 9, 2018 which is based upon and claims the benefit of priority from Japanese Patent Application No. 2017-122540 filed on Jun. 22, 2017; the entire contents of which are incorporated herein by reference.

BACKGROUND

Technical Field

The present disclosure relates to an objective optical system such as an objective optical system for endoscope which can be used in an endoscope apparatus to be used in a medical field and an industrial field, an endoscope, and an image pickup unit.

Description of the Related Art

An endoscope is an apparatus that has been widely used in the medical field and the industrial field. Particularly in the medical field, endoscopes have been used for diagnosis and treatment of parts to be observed. Images achieved by an endoscope inserted into a body cavity are used for the diagnosis and treatment.

In an objective optical system for endoscope, by setting an appropriate F-number and a focusing position, a focused image from a near point up to a far point is formed. Moreover, in an objective optical system, small-sizing of a lens diameter and shortening of an overall length of the optical system have been carried out. By doing so, it is possible to make an insertion portion thin. As a result, it is possible to reduce pain at the time of insertion and to realize an insertion portion that can be turned in a small radius. In recent years, endoscopes of even higher image quality and smaller size have been sought.

As objective optical systems having a small size, objective optical systems described in Japanese Patent No. 3723637 Publication, International Unexamined Patent Application Publication No. 2013/002019, International Unexamined Patent Application Publication No. 2011/145505, Japanese Patent Application Laid-open Publication No. 2001-083400, Japanese Patent Application Laid-open Publication No. Hei 6-222263, Japanese Patent No. 2596810 Publication, and Japanese Patent No. 5927368 Publication are available.

In Japanese Patent No. 3723637 Publication, an image pickup lens has been disclosed. The image pickup lens includes in order from an object side, a negative lens, a positive lens, an aperture stop, a positive lens, a cemented lens in which a negative lens and a positive lens are cemented, and a positive lens.

In International Unexamined Patent Application Publication No. 2013/002019, an endoscope objective optical system has been disclosed. The endoscope objective optical system includes in order from an object side, a negative lens, a positive lens, a meniscus lens that can be inserted and removed, an aperture stop, a positive lens, and a positive lens. The positive lens positioned nearest to an image is cemented to a cover glass of an image sensor.

In International Unexamined Patent Application Publication No. 2011/145505, an endoscope objective lens unit has been disclosed. The endoscope objective lens unit includes in order from an object side, a negative lens, a positive lens, an aperture stop, a positive lens, and a cemented lens in which a positive lens and a negative lens are cemented.

In Japanese Patent Application Laid-open Publication No. 2001-083400, an image pickup optical system has been disclosed. The image pickup optical system includes in order from an object side, a negative lens, a positive lens, an aperture stop, a positive lens, a cemented lens in which a positive lens and a negative lens are cemented, and a positive lens. The positive lens positioned nearest to an image is cemented to a cover glass of an image sensor.

In Japanese Patent Application Laid-open Publication No. Hei 6-222263, an endoscope objective lens has been disclosed. The endoscope objective lens includes in order from an object side, a negative lens, a positive lens, an aperture stop, a positive lens, a cemented lens in which a positive lens and a negative lens are cemented, and a positive lens. The positive lens positioned nearest to an image is cemented to a cover glass of an image sensor.

In Japanese Patent No. 2596810 Publication, an optical system for endoscope has been disclosed. The optical system for endoscope includes in order from an object side, a negative lens, a positive lens, an aperture stop, a positive lens, a cemented lens in which a positive lens and a negative lens are cemented, and a positive lens. The positive lens positioned nearest to an image is cemented to a cover glass of an image sensor.

In Japanese Patent No. 5927368 Publication, an endoscope objective optical system has been disclosed. The endoscope objective optical system includes in order from an object side, a negative lens, a positive lens, an aperture stop, a positive lens, a cemented lens in which a positive lens and a negative lens are cemented, and a positive lens. The positive lens positioned nearest to an image is cemented to a cover glass of an image sensor.

SUMMARY

An objective optical system for endoscope according to at least some embodiments of the present disclosure includes in order from an object side,
a first lens having a negative refractive power,
a second lens having a positive refractive power,
an aperture stop,
a third lens having a positive refractive power,
a fourth lens having a positive refractive power,
a fifth lens having a negative refractive power, and
a sixth lens having a positive refractive power, wherein
the second lens is a meniscus lens having a convex surface directed toward an image side,
the third lens is a meniscus lens having a convex surface directed toward the image side,
a cemented lens having a positive refractive power is formed by the fourth lens and the fifth lens,
the sixth lens is cemented to an image sensor, and
the following conditional expression (1''') is satisfied:

$$1 \leq (r3f + r3r)/(r3f - r3r) \leq 5 \qquad (1''')$$

where,
r3f denotes a radius of curvature of an object-side surface of the third lens, and
r3r denotes a radius of curvature of an image-side surface of the third lens.

An endoscope according to at least some embodiments of the present disclosure includes:

an objective optical system disposed on the distal end portion of an insertion portion which is inserted to an object under examination, and an image sensor disposed on the distal end and receives light from an image of an object formed by the objective optical system, wherein the objective optical system includes in order from an object side, a first lens having a negative refractive power,
a second lens having a positive refractive power,
an aperture stop,
a third lens having a positive refractive power,
a fourth lens having a positive refractive power,
a fifth lens having a negative refractive power, and
a sixth lens having a positive refractive power, wherein the second lens is a meniscus lens having a convex surface directed toward an image side, the third lens is a meniscus lens having a convex surface directed toward the image side, a cemented lens having a positive refractive power is formed by the fourth lens and the fifth lens, the sixth lens is cemented to the image sensor, and the following conditional expression (1''') is satisfied:

$$1 \le (r3f+r3r)/(r3f-r3r) \le 5 \quad (1''')$$

where, r3f denotes a radius of curvature of an object-side surface of the third lens, and r3r denotes a radius of curvature of an image-side surface of the third lens.

An image pickup unit according to at least some embodiments of the present disclosure includes:

an objective optical system which forms an image of an object, and an image sensor which receives light from the image of the object formed by the objective optical system, wherein the objective optical system includes in order from an object side, a first lens having a negative refractive power,
a second lens having a positive refractive power,
an aperture stop,
a third lens having a positive refractive power,
a fourth lens having a positive refractive power,
a fifth lens having a negative refractive power, and
a sixth lens having a positive refractive power, wherein the second lens is a meniscus lens having a convex surface directed toward an image side, the third lens is a meniscus lens having a convex surface directed toward the image side, a cemented lens having a positive refractive power is formed by the fourth lens and the fifth lens, the sixth lens is cemented to the image sensor, and the following conditional expression (1''') is satisfied:

$$1 \le (r3f+r3r)/(r3f-r3r) \le 5 \quad (1''')$$

where, r3f denotes a radius of curvature of an object-side surface of the third lens, and r3r denotes a radius of curvature of an image-side surface of the third lens.

BRIEF DESCRIPTION OF THE DRAWINGS

FIG. 3A is a cross-sectional view of an objective optical system for endoscope of an example 1, and FIG. 3B, FIG. 3C, FIG. 3D, and FIG. 3E are aberration diagrams;

FIG. 4A is a cross-sectional view of an objective optical system for endoscope of an example 2, and FIG. 4B, FIG. 4C, FIG. 4D, and FIG. 4E are aberration diagrams.

FIG. 5A is a cross-sectional view of an objective optical system for endoscope of an example 3, and FIG. 5B, FIG. 5C, FIG. 5D, and FIG. 5E are aberration diagrams.

DETAILED DESCRIPTION

Reasons for adopting such arrangements and effects thereof in an objective optical system for endoscope according to the present embodiment, will be described below by referring to the accompanying diagrams. However, the present disclosure is not restricted to the following embodiment.

An objective optical system for endoscope according to the present embodiment includes in order from an object side, a first lens having a negative refractive power, a second lens having a positive refractive power, an aperture stop, a third lens having a positive refractive power, a fourth lens having a positive refractive power, a fifth lens having a negative refractive power, and a sixth lens having a positive refractive power, wherein the second lens is a meniscus lens having a convex surface directed toward an image side, the third lens is a meniscus lens having a convex surface directed toward the image side, a cemented lens having a positive refractive power is formed by the fourth lens and the fifth lens, the sixth lens is cemented to an image sensor, and the following conditional expression (1) is satisfied:

$$0.55 \le (r3f+r3r)/(r3f-r3r) \le 5 \quad (1)$$

where, r3f denotes a radius of curvature of an object-side surface of the third lens, and r3r denotes a radius of curvature of an image-side surface of the third lens.

Figure 1:
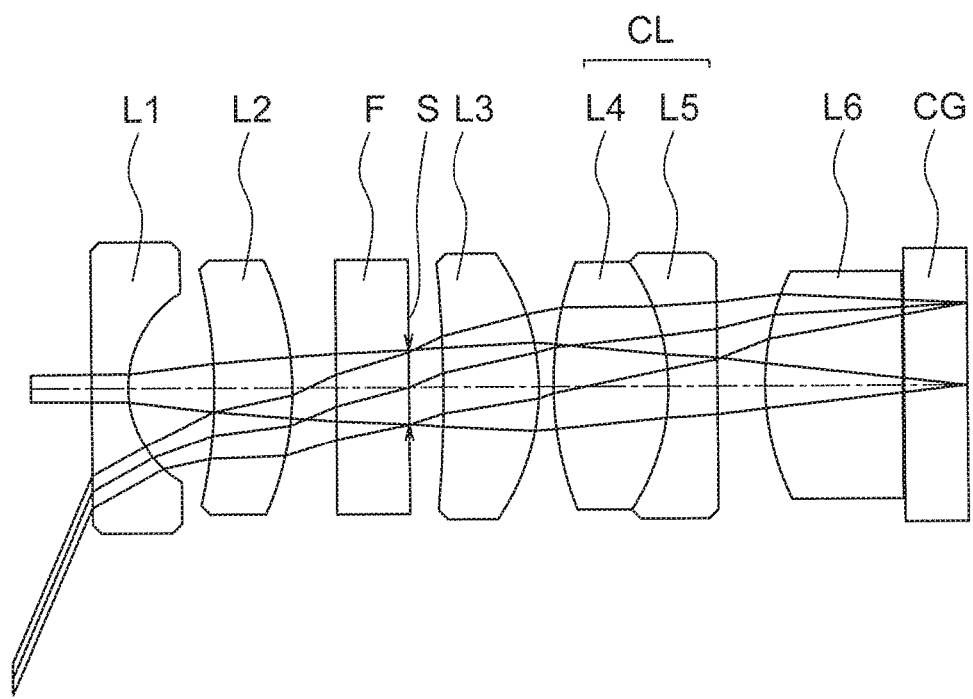
FIG. 1 is a cross-sectional view showing a specific arrangement of an objective optical system for endoscope according to the present embodiment.

The objective optical system for endoscope according to the present embodiment will be described below. FIG. 1 is a cross-sectional view showing the objective optical system for endoscope according to the present embodiment. As shown in FIG. 1, the objective optical system for endoscope according to the present embodiment includes in order from an object side, a first lens L1 having a negative refractive power, a second lens L2 having a positive refractive power, an aperture stop S, a third lens L3 having a positive refractive power, a fourth lens L4 having a positive refractive power, a fifth lens L5 having a negative refractive power, and a sixth lens L6 having a positive refractive power.

The second lens L2 is a meniscus lens having a convex surface directed toward an image side. The third lens L3 is a meniscus lens having a convex surface directed toward the image side. A cemented lens CL having a positive refractive power is formed by the fourth lens L4 and the fifth lens L5. The sixth lens L6 is cemented to a cover glass CG. The cover glass CG is a cover glass of an image sensor. The sixth lens 6, instead of being cemented via the cover glass CG, may be cemented directly to an image pickup surface of the image sensor.

A plane parallel plate F is disposed between the second lens L2 and the third lens L3. It is possible to dispose the plane parallel plate F at an arbitrary position in the objective optical system for endoscope. The cover glass CG is disposed on the image side of the sixth lens L6. The cover glass CG is a cover glass of an image sensor. The image sensor (not shown in the diagram) is disposed on the image side of the cover glass CG. An image-side surface of the cover glass CG is an image plane. The image pickup surface of the image sensor coincides with the image-side surface of the cover glass CG.

The aperture stop S is disposed between the second lens L2 and the third lens L3. More specifically, the aperture stop S is positioned on an image-side surface of the plane parallel plate F.

In an endoscope, generally, it is necessary to able to observe over a wide range. Moreover, since insertion of an insertion portion into a body is carried out, it is necessary that an outer diameter of the insertion portion is thin. For such reason, in an objective optical system for endoscope, an outer diameter of an optical system, and particularly, an outer diameter of a lens positioned nearest to an object has to be made small.

For such reason, in the objective optical system for endoscope according to the present embodiment, as a type of the optical system, an optical system of a retro focus type is adopted. For realizing the optical system of retro focus type, in the objective optical system for endoscope according to the present embodiment, the first lens L1 having a negative refractive power is disposed nearest to the object. Accordingly, a negative refractive power necessary for an optical system of retro focus type has been secured.

The second lens L2 is disposed on the image side of the first lens L1. The second lens L2 is a meniscus lens having a convex surface directed toward the image side. By making such arrangement, an aberration occurred in the first lens L1 having a negative refractive power is corrected in the second lens L2.

The aperture stop S is positioned on the image side of the second lens L2. The third lens L3 is disposed on the image side of the aperture stop S. The third lens L3 is a meniscus lens having a convex surface directed toward the image side. The third lens L3 mainly contributes to image formation. Therefore, in the third lens L3, the positive refractive power necessary for image formation is secured.

The cemented lens CL is disposed on the image side of the third lens L3. The cemented lens CL includes the fourth lens L4 and the fifth lens L5. On the image side of the third lens L3, a height of a light ray reaching a peripheral portion of an image becomes high. It is easy to carry out correction a chromatic aberration at a location at which the height of a light ray is high. Therefore, correction of the chromatic aberration is carried out by disposing the cemented lens CL on the image side of the third lens L3.

Moreover, by making the refractive power of the cemented lens CL a positive refractive power, the positive refractive power necessary for image formation is secured even in the cemented lens CL. In this case, since it is possible to share the positive refractive power necessary for image formation by the third lens L3 and the cemented lens CL, it is possible to suppress both an occurrence of aberration in the third lens L3 and an occurrence of aberration in the cemented lens CL.

The sixth lens L6 is disposed on the image side of the cemented lens CL. The sixth lens L6 is disposed near an image plane.

It is possible to combine the objective optical system for endoscope according to the present embodiment with an image sensor having a small pixel pitch. When the pixel pitch is small, a permissible circle of confusion is also small. As mentioned above, when the permissible circle of confusion in the optical system is small, further higher accuracy is sought for focus adjustment.

In the objective optical system for endoscope according to the present embodiment, the sixth lens L6 is cemented to the cover glass CG. The cover glass CG is a cover glass of the image sensor. Therefore, the sixth lens L6 is integrated with the image sensor via the cover glass CG.

The sixth lens L6 being integrated with the image sensor, The sixth lens L6 is positioned near the image plane. Moreover, the sixth lens L6 has a positive refractive power. Therefore, the sixth lens L6 functions as a field lens. In this case, when the sixth lens L6 and the image sensor are moved together, a longitudinal magnification of the optical system becomes small. Therefore, it is possible to reduce an error sensitivity at the time of focus adjustment. As a result, it is possible to carry out the focus adjustment with high accuracy and ease.

Moreover, the sixth lens L6 has a positive refractive power. Therefore, a principal light ray of a light ray emerged from the sixth lens L6 becomes parallel or almost parallel to a normal of the image plane. Thus, by the sixth lens L6 being disposed near the image plane, an angle made by the principal light ray incident on the image plane and the normal of the image plane becomes small.

The image pickup surface of the image sensor is positioned on the image plane. Moreover, members forming the image sensor are disposed around the image plane. Therefore, light incident on the image plane is reflected at the image pickup surface and the members. The reflected light is redirected toward the optical system. In a case in which the reflected light is not incident on the optical system, there is no problem. However, in a case in which the reflected light is incident on the optical system, there is a possibility that a flare occurs due to the reflected light.

Figure 2A:
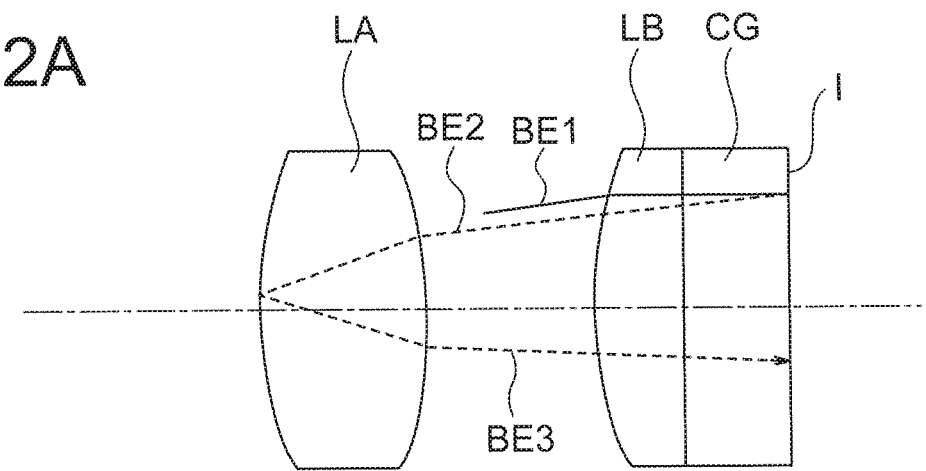
FIG. 2A and FIG. 2B are diagrams showing an appearance of an occurrence of flare.
Figure 2B:
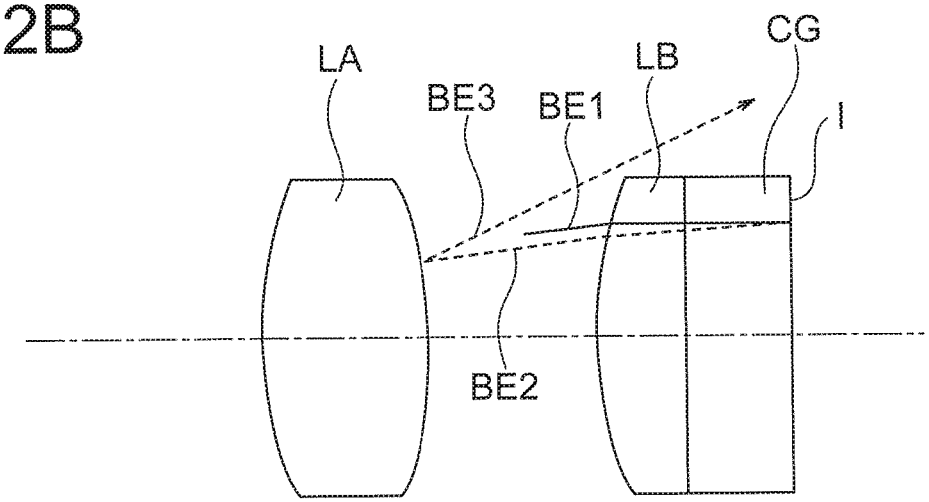

FIG. 2A and FIG. 2B are diagrams showing how the flare occurs. FIG. 2A shows a case in which the flare occurs. FIG. 2B shows a case in which the flare does not occur. In FIG. 2A and FIG. 2B, the light incident on an image plane I is indicated by solid lines, and the light reflected at the image plane I is shown by broken lines.

A light ray BE1 is a light ray directed from a lens LA toward a lens LB, and is a light ray which forms an image of an object. The light ray BE1 passes through the lens LB and the cover glass CG, and reaches the image plane I. The light ray BE1 is reflected by the member disposed on the image plane I. A light ray BE2 is a light ray reflected by the member disposed on the image plane I. The light ray BE2 passes through the cover glass CG and the lens LB, and reaches the lens LA.

At the lens LA, the light ray BE2 is reflected by an object-side surface and an image-side surface. A light ray BE3 is a light ray reflected by the lens surface. The light ray BE3 travels toward the image plane I.

In a case in which the lens LA is a biconvex lens, the object-side surface is a surface which is concave toward the image side. In this case, as shown in FIG. 2A, the light ray BE3 reaches the image-side surface and is refracted at the image-side surface. Therefore, the light ray BE3 passes through the lens LB and the cover glass CG, and reaches the image plane I. Since the light ray BE3 becomes flare light, the flare occurs.

On the other hand, the image-side surface is a surface which is convex toward the image side. In this case, as shown in FIG. 2B, the light ray BE3 travels to a direction away from an optical axis. Therefore, the light ray BE3 does not pass through the lens LB and the cover glass CG, and does not reach the image plane I. Since the light ray BE3 does not become flare light, the flare does not occur.

Because the objective optical system for endoscope according to the present embodiment includes a plurality of lenses, the light ray BE is generated at each lens. Particularly, the third lens L3 is disposed at a position at which the light ray BE3 is susceptible to reach. Therefore, in the objective optical system for endoscope according to the present embodiment, the third lens L3 is a meniscus lens having a convex surface directed toward the image side.

When such arrangement is made, in the third lens L3, both an object-side surface and an image-side surface are surfaces convex toward the image side. Therefore, at both the object-side surface and the image-side surface, it is possible to make the reflected light at the third lens travels to a direction away from the optical axis similarly as in FIG. 2B. As a result, it is possible to suppress the occurrence of flare.

The objective optical system for endoscope according to the present embodiment has the abovementioned arrangement and also conditional expression (1) is satisfied.

In a case of exceeding an upper limit value of conditional expression (1), the radius of curvature of the object-side surface of the third lens becomes excessively small. Consequently, a spherical aberration and a coma are deteriorated.

In a case of falling below a lower limit value of conditional expression (1), the radius of curvature of the image-side surface of the third lens becomes excessively large. In this case, when light reflected by the sixth lens and light reflected by the member disposed on the image plane is reflected at the third lens, the reflected light reaches the image plane as flare light. Consequently, the flare is susceptible to occur.

It is preferable that the following conditional expression (1') be satisfied instead of conditional expression (1).

$$0.9 \leq (r3f + r3r)/(r3f - r3r) \leq 3.5 \quad (1')$$

It is more preferable that the following conditional expression (1") be satisfied instead of conditional expression (1).

$$1.2 \leq (r3f + r3r)/(r3f - r3r) \leq 2 \quad (1'')$$

In the objective optical system for endoscope according to the present embodiment, it is preferable that the following conditional expression (2) be satisfied:

$$-20 \leq r3f/r4f \leq -0.5 \quad (2)$$

where, r3f denotes the radius of curvature of the object-side surface of the third lens, and r4f denotes a radius of curvature of an object-side surface of the fourth lens.

As mentioned above, the third lens is disposed at the position such that the light ray BE3 is susceptible to reach the image plane I. In the fourth lens, since the object-side surface is positioned near the third lens, the arrangement becomes such that the object-side surface of the fourth lens as well is disposed at a position such that the light ray BE3 is susceptible to reach the image plane I. Therefore, it is necessary to take into consideration the occurrence of flare due to the object-side surface of the fourth lens.

However, at the object-side surface of the fourth lens, not only the occurrence of flare but also an occurrence of various aberrations is to be suppressed. By satisfying conditional expression (2), it is possible to correct various aberrations favorably while suppressing the occurrence of flare. As a result, it is possible to suppress degradation of an optical performance.

In a case of exceeding an upper limit value of conditional expression (2), either the radius of curvature of the object-side surface of the third lens becomes excessively large or the radius of curvature of the object-side surface of the fourth lens becomes excessively small. When the radius of curvature of the object-side surface of the third lens becomes excessively large, the flare is susceptible to occur. When the radius of curvature of the object-side surface of the fourth lens becomes excessively small, the spherical aberration and the coma are deteriorated.

In a case of falling below a lower limit value of conditional expression (2), either the radius of curvature of the object-side surface of the third lens becomes excessively small or the radius of curvature of the object-side surface of the fourth lens becomes excessively large. When the radius of curvature of the object-side surface of the third lens becomes excessively small, the spherical aberration and the coma are deteriorated. When the radius of curvature of the object-side surface of the fourth lens becomes excessively large, it becomes difficult to correct favorably the coma and an astigmatism in a peripheral portion of an image.

It is preferable that the following conditional expression (2') be satisfied instead of conditional expression (2).

$$-10 \leq r3f/r4f \leq -0.7 \quad (2')$$

It is more preferable that the following conditional expression (2") be satisfied instead of conditional expression (2).

$$-7 \leq r3f/r4f \leq -1 \quad (2'')$$

For correcting various aberrations favorably, it is preferable to make the fourth lens a biconvex lens. However, when the fourth lens is made a biconvex lens, the object-side surface of the fourth lens becomes a surface which is concave toward the image side. In this case, due to the reflected light at the object-side surface of the fourth lens, the flare is susceptible to occur.

For suppressing the occurrence of flare due to the object-side surface of the fourth lens, it is preferable to make the object-side surface of the fourth lens a surface which is convex toward the image side. However, when such arrangement is made, it is not possible to correct the spherical aberration and the coma.

By satisfying conditional expression (2), even when the object-side surface of the fourth lens is a surface which is concave toward the image side, it is possible to correct the spherical aberration and the coma favorably while suppressing the occurrence of flare.

In the objective optical system for endoscope according to the present embodiment, it is preferable that the following conditional expression (3) be satisfied:

$$-1 \leq r6f/r3f \leq -0.02 \quad (3)$$

where, r6f denotes a radius of curvature of an object-side surface of the sixth lens, and r3f denotes the radius of curvature of the object-side surface of the third lens.

In the objective optical system for endoscope according to the present embodiment, the object-side surface of the third lens and the object-side surface of the sixth lens are instrumental in an image forming position of the flare light. Moreover, the sixth lens is instrumental in an error sensitivity at the time of focus adjustment. By satisfying conditional expression (3), it is possible to set appropriately both the radius of curvature of the object-side surface of the third lens and the radius of curvature of the object-side surface of the sixth lens. As a result, it is possible to lower the error sensitivity at the time of focus adjustment while suppressing the occurrence of flare.

In a case of exceeding an upper limit value of conditional expression (3), either the radius of curvature of the object-side surface of the sixth lens becomes excessively small or the radius of curvature of the object-side surface of the third lens becomes excessively large. When the radius of curvature of the object-side surface of the sixth lens becomes excessively small, a curvature of field is corrected excessively. When the radius of curvature of the object-side surface of the third lens becomes excessively large, the flare is susceptible to occur.

In a case of falling below a lower limit value of conditional expression (3), either the radius of curvature of the object-side surface of the sixth lens becomes excessively large or the radius of curvature of the object-side surface of the third lens becomes excessively small. When the radius of curvature of the object-side surface of the sixth lens becomes excessively large, a focal shift due to a manufacturing error becomes large. Moreover, since light reflected at the sixth lens is susceptible to reach the third lens, the flare is susceptible to occur. When the radius of curvature of the object-side surface of the third lens becomes excessively small, the spherical aberration and the coma are deteriorated.

It is more preferable that the following conditional expression (3') be satisfied instead of conditional expression (3).

$$-0.7 \le r6f/r3fs \le -0.05 \qquad (3')$$

It is even more preferable that the following conditional expression (3") be satisfied instead of conditional expression (3).

$$-0.5 \le r6f/r3fs \le -0.1 \qquad (3'')$$

In the objective optical system for endoscope according to the present embodiment, it is preferable that the following conditional expression (4) be satisfied:

$$-0.7 \le f1/f4 \le -0.3 \qquad (4)$$

where, f1 denotes a focal length of the first lens, and
f4 denotes a focal length of the fourth lens.

In an optical system of retro focus type, the overall length of the optical system tends to become long. For suppressing an increase in the overall length of the optical system and deterioration of aberration, it is necessary to set appropriately both the refractive power of a negative lens and the refractive power of a positive lens. In the objective optical system for endoscope according to the present embodiment, the optical system of retro focus type is formed by the first lens having a negative refractive power and the fourth lens having a positive refractive power. By satisfying conditional expression (4), it is possible to suppress the increase in the overall length of the optical system and the deterioration of aberration.

In a case of exceeding an upper limit value of conditional expression (4), either the focal length of the first lens becomes excessively large or the focal length of the fourth lens becomes excessively small. When the focal length of the first lens becomes excessively large, the overall length of the optical system becomes long. When the focal length of the fourth lens becomes excessively small, the spherical aberration and the coma are deteriorated.

In a case of falling below a lower limit value of conditional expression (4), either the focal length of the first lens becomes excessively small or the focal length of the fourth lens becomes excessively large. When the focal length of the first lens becomes excessively small, the coma and the astigmatism are deteriorated. When the focal length of the fourth lens becomes excessively large, the overall length of the optical system becomes large.

It is more preferable that the following conditional expression (4') be satisfied instead of conditional expression (4).

$$-0.68 \le f1/f4 \le -0.35 \qquad (4')$$

It is even more preferable that the following conditional expression (4") be satisfied instead of conditional expression (4).

$$-0.65 \le f1/f4 \le -0.4 \qquad (4'')$$

As mentioned above, for correcting various aberrations favorably, it is preferable to make the fourth lens a biconvex lens. Whereas, for suppressing the occurrence of flare due to the object-side surface of the fourth lens, it is preferable to make the object-side surface of the fourth lens a surface which is convex on the image side.

However, when the object-side surface of the fourth lens is made a surface which is convex toward the image side, a shape of the fourth lens becomes a meniscus shape. In this case, when the positive refractive power of the fourth lens is made large, the imaging performance is degraded.

By satisfying conditional expression (4), even when the object-side surface of the fourth lens is a surface which is concave toward the image side, it is possible to prevent the degradation of imaging performance while suppressing the occurrence of flare.

In the objective optical system for endoscope according to the present embodiment, it is preferable that the following conditional expression (5) be satisfied:

$$0.6 \le r3r/r4r \le 1.7 \qquad (5)$$

where, r3r denotes the radius of curvature of the image-side surface of the third lens, and
r4r denotes a radius of curvature of an image-side surface of the fourth lens.

As mentioned above, the occurrence of flare has to be suppressed at the object-side surface of the third lens and the object-side surface of the fourth lens. Therefore, setting of the radius of curvature of the object-side surface of the third lens and setting of the radius of curvature of the object-side surface of the fourth lens are restricted to some extent. This signifies that it is not possible to use the object-side surface of the third lens and the object-side surface of the fourth lens only for aberration correction.

Therefore, the image-side surface of the third lens and the image-side surface of the fourth lens play a role in aberration correction at the third lens and aberration correction at the fourth lens. By satisfying conditional expression (5), it is possible to correct various aberrations favorably. As a result, it is possible to suppress degradation of an optical performance.

In a case of exceeding an upper limit value of conditional expression (5), either the radius of curvature of the image-side surface of the third lens becomes excessively large or the radius of curvature of the image-side surface of the fourth lens becomes excessively small. When the radius of curvature of the image-side surface of the third lens becomes excessively large, either the spherical aberration and the coma are corrected inadequately or the overall length of the optical system becomes long. When the radius of curvature of the image-side surface of the fourth lens becomes excessively small, the coma, the astigmatism, and a chromatic aberration are corrected excessively.

In a case of falling below a lower limit value of conditional expression (5), either the radius of curvature of the image-side surface of the third lens becomes excessively small or the radius of curvature of the image-side surface of the fourth lens becomes excessively large. When the radius of curvature of the image-side surface of the third lens becomes excessively small, the spherical aberration and the coma are corrected excessively. When the radius of curvature of the image-side surface of the fourth lens becomes excessively large, the coma, the astigmatism, and the chromatic aberration are corrected inadequately.

It is more preferable that the following conditional expression (5') be satisfied instead of conditional expression (5).

$$0.7 \leq r3r/r4r \leq 1.5 \quad (5')$$

It is even more preferable that the following conditional expression (5") be satisfied instead of conditional expression (5).

$$0.8 \leq r3r/r4r \leq 1.3 \quad (5'')$$

In the objective optical system for endoscope according to the present embodiment, it is preferable that the following conditional expression (6) be satisfied:

$$-0.7 \leq (r3r+r4f)/(r3r-r4f) \leq -0.1 \quad (6)$$

where,
r3r denotes the radius of curvature of the image-side surface of the third lens, and
r4f denotes the radius of curvature of the object-side surface the fourth lens.

In the objective optical system for endoscope according to the present embodiment, the image-side surface of the third lens is instrumental in the positive refractive power of the overall optical system and the object-side surface of the fourth lens is instrumental in the occurrence of flare. BY satisfying conditional expression (6), it is possible to set appropriately both the radius of curvature of the image-side surface of the third lens and the radius of curvature of the object-side surface of the fourth lens. As a result, it is possible to suppress the occurrence of flare while maintaining appropriately the positive refractive power of the overall optical system.

In a case of exceeding an upper limit value of conditional expression (6), the radius of curvature of the object-side surface of the fourth lens becomes excessively small. Consequently, the flare is susceptible to occur. In a case of falling below a lower limit value of conditional expression (6), the radius of curvature of the image-side surface of the third lens becomes excessively small. Consequently, the spherical aberration and the coma are deteriorated.

It is more preferable that the following conditional expression (6') be satisfied instead of conditional expression (6).

$$-0.5 \leq (r3r+r4f)/(r3r-r4f) \leq -0.18 \quad (6')$$

It is even more preferable that the following conditional expression (6") be satisfied instead of conditional expression (6).

$$-0.35 \leq (r3r+r4f)/(r3r-r4f) \leq -0.18 \quad (6'')$$

In the objective optical system for endoscope according to the present embodiment, it is preferable that the following conditional expression (7) be satisfied:

$$0.05 \leq (r4f+r4r)/(r4f-r4r) \leq 0.33 \quad (7)$$

where,
r4f denotes the radius of curvature of the object-side surface of the fourth lens, and
r4r denotes the radius of curvature of the image-side surface of the fourth lens.

In the objective optical system for endoscope according to the present embodiment, the object-side surface of the fourth is instrumental in the occurrence of flare and the image-side surface of the fourth lens is instrumental in an aberration which is remarkable in a peripheral portion of an image, for example the chromatic aberration and the coma. By satisfying conditional expression (7), it is possible to set appropriately both the radius of curvature of the object-side surface and the radius of curvature of the image-side surface. As a result, it is possible to correct favorably the aberration which is remarkable in the peripheral portion of the image, for example the chromatic aberration and the coma, while suppressing the occurrence of flare.

In a case of exceeding an upper limit value of conditional expression (7), the radius of curvature of the image-side surface becomes excessively small. Consequently, the chromatic aberration and the coma are corrected excessively. In a case of falling below a lower limit value of conditional expression (7), the radius of curvature of the object-side surface becomes excessively small. Consequently, the flare is susceptible to occur.

It is more preferable that the following conditional expression (7') be satisfied instead of conditional expression (7).

$$0.1 \leq (r4f+r4r)/(r4f-r4r) \leq 0.29 \quad (7')$$

In the objective optical system for endoscope according to the present embodiment, it is preferable that the following conditional expression (8) be satisfied:

$$-1.45 \leq f3/f5 \leq -1 \quad (8)$$

where,
f3 denotes a focal length of the third lens, and
f5 denotes a focal length of the fifth lens.

In the objective optical system for endoscope according to the present embodiment, the positive refractive power of the third lens and the negative refractive power of the fifth lens are instrumental in an aberration which is remarkable in a peripheral portion of an image, for example the coma and the astigmatism. By satisfying conditional expression (8) it is possible to balance the positive refractive power of the third lens and the negative refractive power the fifth lens. As a result, it is possible to correct favorably the aberration which is remarkable in the peripheral portion of the image, for example the coma and the astigmatism.

In a case of exceeding an upper limit value of conditional expression (8), either the focal length of the third lens becomes excessively small or the focal length of the fifth lens becomes excessively large. When the focal length of the third lens becomes excessively small, correction of the coma and the astigmatism are corrected excessively. When the focal length of the fifth lens becomes excessively large, the coma and the astigmatism are corrected inadequately.

In a case of falling below a lower limit value of conditional expression (8), either the focal length of the third lens becomes excessively large or the focal length of the fifth lens becomes excessively small. When the focal length of the third lens becomes excessively large, either the overall length of the optical system becomes long or the coma and the astigmatism are corrected inadequately. When the focal length of the fifth lens becomes excessively small, the coma and the astigmatism are corrected excessively.

It is more preferable that the following conditional expression (8') be satisfied instead of conditional expression (8).

$$-1.4 \leq f3/f5 \leq -1.1 \quad (8')$$

In the objective optical system for endoscope according to the present embodiment, it is preferable that the following conditional expression (9-1) be satisfied:

$$-2.5 \leq r6f/r3r \leq -0.65 \quad (9\text{-}1)$$

where,
r6f denotes a radius of curvature of an object-side surface of the sixth lens, and
r3r denotes the radius of curvature of the image-side surface of the third lens.

In a case of exceeding an upper limit value of conditional expression (9-1), either the radius of curvature of the object-side surface of the sixth lens becomes excessively small or the radius of curvature of the image-side surface of the third lens becomes excessively large. When the radius of curvature of the object-side surface of the sixth lens becomes excessively small, the astigmatism and the curvature of field are deteriorated. When the radius of curvature of the image-side surface of the third lens becomes excessively large, either the overall length of the optical system becomes long or the coma is corrected inadequately.

In a case of falling below a lower limit value of conditional expression (9-1), either the radius of curvature of the object-side surface of the sixth lens becomes excessively large or the radius of curvature of the image-side surface of the third lens becomes excessively small. When the radius of curvature of the object-side surface of the sixth lens becomes excessively large, an effect of focal shift due to a manufacturing error becomes large. When the radius of curvature of the image-side surface of the third lens becomes excessively small, the coma is corrected excessively.

It is more preferable that the following conditional expression (9-1') be satisfied instead of conditional expression (9-1).

$$-2 \leq r6f/r3r \leq -0.8 \quad (9\text{-}1')$$

In the objective optical system for endoscope according to the present embodiment, it is preferable that the following conditional expression (9-2) be satisfied:

$$1.5 \leq f2/f3 \leq 3 \quad (9\text{-}2)$$

where,
f2 denotes a focal length of the second lens, and
f3 denotes the focal length of the third lens.

In an optical system in which a lens is disposed on both sides of an aperture stop, a balance of refractive power of the lens on one side and refractive power of the lens on the other side is instrumental in an aberration which is remarkable in a peripheral portion of an image. In the objective optical system for endoscope according to the present embodiment, the balance of the refractive power of the second lens and the refractive power of the third lens is instrumental in an aberration which is remarkable in the peripheral portion of the image. By satisfying conditional expression (9-2), it is possible to balance the refractive power of the second lens and the refractive power of the third lens. As a result, it is possible to correct favorably an aberration which is remarkable in the peripheral portion of the image.

In a case of exceeding an upper limit value of conditional expression (9-2), either the focal length of the second lens becomes excessively large or the focal length of the third lens becomes excessively small. When the focal length of the second lens becomes excessively large, the coma, the astigmatism and a chromatic aberration of magnification are corrected inadequately. When the focal length of the third lens becomes excessively small, the coma is corrected excessively.

In a case of exceeding falling below a lower limit value of conditional expression (9-2), either the focal length of the second lens becomes excessively small or the focal length of the third lens becomes excessively large. When the focal length of the second lens becomes excessively small, the coma, the astigmatism, and the chromatic aberration of magnification are corrected excessively. When the focal length of the third lens becomes excessively large, either the overall length of the optical system becomes long, or the coma is corrected inadequately.

It is more preferable that the following conditional expression (9-2') be satisfied instead of conditional expression (9-2).

$$1.6 \leq f2/f3 \leq 2.9 \quad (9\text{-}2')$$

In the objective optical system for endoscope according to the present embodiment, it is preferable that the following conditional expression (10-1) and (10-2) be satisfied:

$$-0.25 \leq (r5f+r6f)/(r5f-r6f) \leq 0.2 \quad (10\text{-}1)$$

$$1 \leq f2/f6 \leq 1.6 \quad (10\text{-}2)$$

where,
r5f denotes a radius of curvature of an object-side surface of the fifth lens,
r6f denotes the radius of curvature of the object-side surface of the sixth lens,
f2 denotes the focal length of the second lens, and
f6 denotes a focal length of the sixth lens.

As mentioned above, the sixth lens is integrated with the image sensor via the cover glass. At the time of focus adjustment, by the sixth lens and the image sensor moving integrally, it is possible to decrease the error sensitivity at the time of focus adjustment. When an effect of decreasing the error sensitivity is enhanced, an effect on imaging performance in a peripheral portion of an image also becomes large.

The sixth lens exerts an influence on the effect of decreasing the error sensitivity. Therefore, it is preferable to balance the refractive power and shape of a lens surface by the sixth lens and another lens. By satisfying conditional expressions (10-1) and (10-2), it is possible to suppress degradation of imaging performance in the peripheral portion of the image while achieving the effect of decreasing the error sensitivity.

In a case of exceeding an upper limit value of conditional expression (10-1), either the radius of curvature of the object-side surface of the fifth lens becomes excessively large or the radius of curvature of the object-side surface of the sixth lens becomes excessively small. When the radius of curvature of the object-side surface of the fifth lens becomes excessively large, the chromatic aberration is corrected inadequately. When the radius of curvature of the object-side surface of the sixth lens becomes excessively small, the curvature of field is corrected excessively.

In a case of falling below a lower limit value of conditional expression (10-1), either the radius of curvature of the object-side surface of the fifth lens becomes excessively small or the radius of curvature of the object-side surface of the sixth lens becomes excessively large. When the radius of curvature of the object-side surface of the fifth lens becomes excessively small, the chromatic aberration is corrected excessively. When the radius of curvature of the object-side surface of the sixth lens becomes excessively large, an effect of focal shift due to a manufacturing error is enhanced.

In a case of exceeding an upper limit value of conditional expression (10-2), either the focal length of the second lens becomes excessively large or the focal length of the sixth lens becomes excessively small. When the focal length of the second lens becomes excessively large, the correction of the astigmatism, the coma, and the chromatic aberration becomes inadequate. When the focal length of the sixth lens is excessively small, the curvature of field and the coma are deteriorated.

In a case of falling below a lower limit value of conditional expression (10-2), either the focal length of the second lens becomes excessively small or the focal length of the sixth lens becomes excessively large. When the focal length of the second lens becomes excessively small, the astigmatism, the coma, and the chromatic aberration are corrected excessively. When the focal length of the sixth lens becomes excessively large, the effect of focal shift due to a manufacturing error is enhanced.

It is more preferable that the following conditional expression (10-1') be satisfied instead of conditional expression (10-1).

$$-0.18 \leq (r5f + r6f)/(r5f - r6f) \leq 0.15 \quad (10\text{-}1')$$

It is more preferable that the following conditional expression (10-2') be satisfied instead of conditional expression (10-2).

$$1.1 \leq f2/f6 \leq 1.5 \quad (10\text{-}2')$$

In the objective optical system for endoscope according to the present embodiment, it is preferable that the following conditional expression (11) be satisfied:

$$-15 \leq f45/f1 \leq -3 \quad (11)$$

where, f45 denotes a focal length of the cemented lens, and
f1 denotes the focal length of the first lens.

Since the cemented lens has a positive refractive power, it is possible to realize an optical system of retro focus type by a combination with the negative refractive power of the first lens. By maintaining the positive refractive power of the cemented lens appropriately, it is possible to form an optical system of retro focus type, together with the negative refractive power of the first lens.

A large part of the negative refractive power which is necessary for the optical system of retro focus type is borne by the first lens. The negative refractive power of the first lens being large, a comparatively large aberration occurs at the first lens. Therefore, it is necessary to correct appropriately the aberration that occurred at the first lens by the cemented lens which is positioned on the image side and across the aperture stop. By satisfying conditional expression (11), it is possible to correct favorably the aberration occurred in the first lens.

In a case of exceeding an upper limit value of conditional expression (11), either the focal length of the cemented lens become excessively small or the focal length of the first lens becomes excessively large. When the focal length of the cemented lens becomes excessively small, the chromatic aberration is corrected excessively. When the focal length of the first lens becomes excessively large, the overall length of the optical system becomes long.

In a case of falling below a lower limit value of conditional expression (11), either the focal length of the cemented lens becomes excessively large or the focal length of the first lens becomes excessively small. When the focal length of the cemented lens becomes excessively large, the chromatic aberration is corrected inadequately. When the focal length of the first lens becomes excessively small, the coma and the astigmatism are deteriorated.

It is more preferable that the following conditional expression (11') be satisfied instead of conditional expression (11).

$$-13.5 \leq f45/f1 \leq -4 \quad (11')$$

It is even more preferable that the following conditional expression (11") be satisfied instead of conditional expression (11).

$$-12 \leq f45/f1 \leq -5 \quad (11'')$$

Moreover, in the objective optical system for endoscope of the present embodiment, it is preferable to make the following arrangement for the first lens. During observation, dirt and blood are adhered to the object-side surface of the first lens. In this state, it is not possible to carryout clear observation. Therefore, cleaning of the object-side surface of the first lens is carried out by water from a nozzle at a front end of an insertion portion.

When the object-side surface of the first lens has a convex shape, it is difficult to remove the dirt at the time of cleaning. Moreover, when the object-side surface of the first lens has a concave shape, water is accumulated in the concave shape. Particularly, when the object-side surface of the first lens has a convex shape, a scratch or a crack due to a shock is susceptible occur. Therefore, it is preferable that the shape of the first lens be planoconcave with a flat surface directed toward the object side.

Examples of objective optical systems for endoscope will be described below in detail by referring to the accompanying diagrams. However, the present invention is not restricted to the examples described below.

A lens cross-sectional view of each example will be described below. FIG. 3A, FIG. 4A, and FIG. 5A show lens cross-sectional views.

Aberration diagrams of each example will be described below.

FIG. 3B, FIG. 4B, and FIG. 5B show a spherical aberration (SA).

FIG. 3C, FIG. 4C, and FIG. 5C show an astigmatism (AS).

FIG. 3D, FIG. 4D, and FIG. 5D show a distortion (DT).

FIG. 3E, FIG. 4E, and FIG. 5E show a chromatic aberration of magnification (CC).

In each aberration diagram, a horizontal axis indicates an aberration amount. For the spherical aberration, the astigmatism, and the chromatic aberration of magnification, the unit of aberration amount is mm. Moreover, for the distortion, the unit of aberration amount is %. Moreover, FIY denotes an image height and the unit thereof is mm, and FNO denotes an F-number. Furthermore, the unit of wavelength of an aberration curve is nm.

Example 1

An objective optical system for endoscope according to an example 1 will be described below. The objective optical system for endoscope of the example 1 includes in order from an object side, a planoconcave negative lens L1, a positive meniscus lens L2 having a convex surface directed toward an image side, a positive meniscus lens L3 having a convex surface directed toward the image side, a biconvex positive lens L4, a planoconcave negative lens L5, and a planoconvex positive lens L6. Here, the biconvex positive lens L4 and the planoconcave negative lens L5 are cemented.

An aperture stop S is positioned between the positive meniscus lens L2 and the positive meniscus lens L3. A plane parallel plate F is disposed between the positive meniscus lens L2 and the positive meniscus lens L3. The aperture stop S is positioned on an image-side surface of the plane parallel plate F. The plane parallel plate F is an infrared absorbing filter.

A cover glass CG is disposed on the image side of the planoconvex positive lens L6. The planoconvex positive lens L6 and the cover glass CG are cemented. The cover glass CG is a cover glass of an image sensor.

Example 2

An objective optical system for endoscope according to an example 2 will be described below. The objective optical system for endoscope of the example 2 includes in order from an object side, a planoconcave negative lens L1, a positive meniscus lens L2 having a convex surface directed toward an image side, a positive meniscus lens L3 having a convex surface directed toward the image side, a biconvex positive lens L4, a negative meniscus lens L5 having a convex surface directed toward the image side, and a planoconvex positive lens L6. Here, the biconvex positive lens L4 and the negative meniscus lens L5 are cemented.

An aperture stop S is positioned between the positive meniscus lens L2 and the positive meniscus lens L3. A plane parallel plate F is disposed between the positive meniscus lens L2 and the positive meniscus lens L3. The aperture stop S is positioned on an image-side surface of the plane parallel plate F. The plane parallel plate F is an infrared absorbing filter.

A cover glass CG is disposed on the image side of the planoconvex positive lens L6. The planoconvex positive lens L6 and the cover glass CG are cemented. The cover glass CG is a cover glass of an image sensor.

Example 3

An objective optical system for endoscope according to an example 3 will be described below. The objective optical system for endoscope of the example 3 includes in order from an object side, a planoconcave negative lens L1, a positive meniscus lens L2 having a convex surface directed toward an image side, a positive meniscus lens L3 having a convex surface directed toward the image side, a biconvex positive lens L4, a negative meniscus lens L5 having a convex surface directed toward the image side, and a planoconvex positive lens L6. Here, the biconvex positive lens L4 and the negative meniscus lens L5 are cemented.

An aperture stop S is positioned between the positive meniscus lens L2 and the positive meniscus lens L3. A plane parallel plate F is disposed between the positive meniscus lens L2 and the positive meniscus lens L3. The aperture stop S is positioned on an image-side surface of the plane parallel plate F. The plane parallel plate F is an infrared absorbing filter.

A cover glass CG is disposed on the image side of the planoconvex positive lens L6. The planoconvex positive lens L6 and the cover glass CG are cemented. The cover glass CG is a cover glass of an image sensor.

Numerical data of each example described above is shown below. In Surface data, r denotes radius of curvature of each lens surface, d denotes a distance between respective lens surfaces, ne denotes a refractive index of each lens for a e-line, and vd denotes an Abbe number for each lens.

Moreover, in Various data, Fno denotes an F number, ω denotes a half angle of view, and IH denotes an image height.

Example 1

Unit mm

Surface data

| Surface no. | r | d | ne | vd |
|---|---|---|---|---|
| 1 | ∞ | 0.2227 | 1.88815 | 40.76 |
| 2 | 0.6837 | 0.5233 | | |
| 3 | −3.1793 | 0.4788 | 1.97189 | 17.47 |
| 4 | −1.8898 | 0.2673 | | |
| 5 | ∞ | 0.4454 | 1.49557 | 75.00 |
| 6 | ∞ | 0.0000 | | |
| 7(Stop) | ∞ | 0.2116 | | |
| 8 | −7.9376 | 0.5902 | 1.88815 | 40.76 |
| 9 | −1.4053 | 0.0891 | | |
| 10 | 2.1058 | 0.7016 | 1.69979 | 55.53 |
| 11 | −1.3563 | 0.3007 | 1.97189 | 17.47 |
| 12 | ∞ | 0.2906 | | |
| 13 | 1.6281 | 0.8352 | 1.51825 | 64.14 |
| 14 | ∞ | 0.0100 | 1.51500 | 64.00 |
| 15 | ∞ | 0.3898 | 1.50700 | 63.26 |
| 16 | ∞ | 0.0000 | | |
| Image plane | ∞ | | | |

Various data

| | |
|---|---|
| Fno | 2.97 |
| ω | 66.3° |
| IH | 0.5 mm |

Example 2

Unit mm

Surface data

| Surface no. | r | d | ne | vd |
|---|---|---|---|---|
| 1 | ∞ | 0.2372 | 1.88815 | 40.76 |
| 2 | 0.6418 | 0.5346 | | |
| 3 | −3.1017 | 0.4000 | 1.97189 | 17.47 |
| 4 | −1.8160 | 0.2059 | | |
| 5 | ∞ | 0.4400 | 1.49557 | 75.00 |
| 6 | ∞ | 0.0000 | | |
| 7(Stop) | ∞ | 0.2007 | | |
| 8 | −11.3385 | 0.6000 | 1.88815 | 40.76 |
| 9 | −1.5047 | 0.1042 | | |
| 10 | 2.2678 | 0.7012 | 1.69979 | 55.53 |
| 11 | −1.2720 | 0.3018 | 1.97189 | 17.47 |
| 12 | −10.0055 | 0.3348 | | |
| 13 | 1.6494 | 0.8911 | 1.51825 | 64.14 |
| 14 | ∞ | 0.0100 | 1.51500 | 64.00 |
| 15 | ∞ | 0.3898 | 1.50700 | 63.26 |
| 16 | ∞ | 0.0000 | | |
| Image plane | ∞ | | | |

Various data

| | |
|---|---|
| Fno | 2.96 |
| ω | 66.0° |
| IH | 0.5 mm |

Example 3

| Unit mm | | | | |
|---|---|---|---|---|
| Surface data | | | | |
| Surface no. | r | d | ne | vd |
| 1 | ∞ | 0.2326 | 1.88815 | 40.76 |
| 2 | 0.6675 | 0.4938 | | |
| 3 | −12.6752 | 0.4994 | 1.97189 | 17.47 |
| 4 | −2.6882 | 0.1172 | | |
| 5 | ∞ | 0.4454 | 1.49557 | 75.00 |
| 6 | ∞ | 0.0000 | | |
| 7(Stop) | ∞ | 0.1980 | | |
| 8 | −4.2927 | 0.5991 | 1.88815 | 40.76 |
| 9 | −1.3857 | 0.0921 | | |
| 10 | 2.1456 | 0.6994 | 1.69979 | 55.53 |
| 11 | −1.4128 | 0.3001 | 1.97189 | 17.47 |
| 12 | −19.0871 | 0.2027 | | |
| 13 | 1.3844 | 1.0779 | 1.51825 | 64.14 |
| 14 | ∞ | 0.0100 | 1.51500 | 64.00 |
| 15 | ∞ | 0.3898 | 1.50700 | 63.26 |
| 16 | ∞ | 0.0000 | | |
| Image plane | ∞ | | | |

| Various data | |
|---|---|
| Fno | 2.81 |
| ω | 66.2° |
| IH | 0.5 mm |

Next, the values of conditional expressions (1) to (11) in the objective optical system for endoscope according to examples 1 to 3 are shown below.

| Conditional expression | Example1 | Example2 | Example3 |
|---|---|---|---|
| (1) (r3f + r3r)/(r3f − r3r) | 1.43 | 1.31 | 1.95 |
| (2) r3f/r4f | −3.77 | −5.00 | −2.00 |
| (3) r6f/r3f | −0.21 | −0.15 | −0.32 |
| (4) f1/f4 | −0.60 | −0.57 | −0.57 |
| (5) r3r/r4r | 1.04 | 1.18 | 0.98 |
| (6) (r3r + r4f)/(r3r − r4f) | −0.20 | −0.20 | −0.22 |
| (7) (r4f + r4r)/(r4f − r4r) | 0.22 | 0.28 | 0.21 |
| (8) f3/f5 | −1.32 | −1.24 | −1.33 |
| (9-1) r6f/r3r | −1.16 | −1.10 | −1.00 |
| (9-2) f2/f3 | 2.20 | 2.06 | 1.63 |
| (10-1) (r5f + r6f)/(r5f − r6f) | −0.09 | −0.13 | 0.01 |
| (10-2) f2/f6 | 1.29 | 1.23 | 1.28 |
| (11) f45/f1 | −8.16 | −6.76 | −6.58 |

According to the examples, it is possible to provide an objective optical system for endoscope having a small F-number, a small size, and a high imaging performance, which is strong against manufacturing error and in which it is easy to suppress an occurrence of flare.

The embodiment and various examples of the present disclosure are described above. However, the present disclosure is not restricted to these embodiment and examples, and embodiments formed by combining arrangement of these embodiment and examples without departing from the scope of the present disclosure are also included in the category of the present disclosure.

According to the present embodiment, it is possible to provide an objective optical system for endoscope having a small F-number, a small size, and a high imaging performance, which is strong against manufacturing error, and in which it is easy to suppress an occurrence of flare.

As described heretofore, the present disclosure is suitable for an objective optical system for endoscope having a small F-number, a small-size, and a high imaging performance, which is strong against manufacturing error, and in which it is easy to suppress an occurrence of flare.

What is claimed is:

1. An objective optical system for an endoscope, the objective optical system consisting of, in order from an object side:
   a first lens having a negative refractive power,
   a second lens having a positive refractive power,
   an aperture stop,
   a third lens having a positive refractive power,
   a fourth lens having a positive refractive power,
   a fifth lens having a negative refractive power, and
   a sixth lens having a positive refractive power,
   wherein:
   the second lens is a meniscus lens having a convex surface directed toward an image side,
   the third lens is a meniscus lens having a convex surface directed toward the image side,
   a cemented lens having a positive refractive power is formed by the fourth lens and the fifth lens,
   the sixth lens is cemented to an image sensor, and
   the following conditional expressions (1''') and (7) are satisfied:

$$1 \leq (r3f + r3r)/(r3f - r3r) \leq 5 \tag{1'''}$$

$$0.05 \leq (r4f + r4r)/(r4f - r4r) \leq 0.33 \tag{7}$$

where,
r3f denotes a radius of curvature of an object-side surface of the third lens,
r3r denotes a radius of curvature of an image-side surface of the third lens,
r4f denotes a radius of curvature of the object-side surface of the fourth lens, and
r4r denotes a radius of curvature of the image-side surface of the fourth lens.

2. The objective optical system according to claim 1, wherein the following conditional expression (2) is satisfied:

$$-20 \leq r3f/r4f \leq -0.5 \tag{2}$$

3. The objective optical system according to claim 1, wherein the following conditional expression (3) is satisfied:

$$-1 \leq r6f/r3f \leq -0.02 \tag{3}$$

where r6f denotes a radius of curvature of an object-side surface of the sixth lens.

4. The objective optical system according to claim 1, wherein the following conditional expression (4) is satisfied:

$$-0.7 \leq f1/f4 \leq -0.3 \tag{4}$$

where,
f1 denotes a focal length of the first lens, and
f4 denotes a focal length of the fourth lens.

5. The objective optical system according to claim 1, wherein the following conditional expression (5) is satisfied:

$$0.6 \leq r3r/r4r \leq 1.7 \tag{5}$$

6. The objective optical system according to claim 1, wherein the following conditional expression (6) is satisfied:

$$-0.7 \leq (r3r + r4f)/(r3r - r4f) \leq -0.1 \tag{6}$$

7. The objective optical system according to claim 1, wherein the following conditional expressions (9-1) and (9-2) are satisfied:

$$-2.5 \leq r6f/r3r \leq -0.65 \tag{9-1}$$

$$1.5 \leq f2/f3 \leq 3 \tag{9-2}$$

where,
r6f denotes a radius of curvature of an object-side surface of the sixth lens,
f2 denotes a focal length of the second lens, and
f3 denotes a focal length of the third lens.

8. The objective optical system according to claim 1, wherein the following conditional expressions (10-1) and (10-2) are satisfied:

$$-0.25 \leq (r5f+r6f)/(r5f-r6f) \leq 0.2 \tag{10-1}$$

$$1 \leq f2/f6 \leq 1.6 \tag{10-2}$$

where,
r5f denotes a radius of curvature of an object-side surface of the fifth lens,
r6f denotes a radius of curvature of the object-side surface of the sixth lens,
f2 denotes a focal length of the second lens, and
f6 denotes a focal length of the sixth lens.

9. An endoscope comprising:
the objective optical system according to claim 1, the objective optical system being disposed at a distal end portion of an insertion portion which is insertable into an object under examination, and
an image sensor that is disposed at the distal end portion and that receives light from an image of the object formed by the objective optical system.

10. An image pickup unit comprising:
the objective optical system according to claim 1, which forms an image of an object, and
an image sensor which receives light from the image of the object formed by the objective optical system.

11. An objective optical system for an endoscope, the objective optical system consisting of, in order from an object side:
a first lens having a negative refractive power,
a second lens having a positive refractive power,
an aperture stop,
a third lens having a positive refractive power,
a fourth lens having a positive refractive power,
a fifth lens having a negative refractive power, and
a sixth lens having a positive refractive power,
wherein:
the second lens is a meniscus lens having a convex surface directed toward an image side,
the third lens is a meniscus lens having a convex surface directed toward the image side,
a cemented lens having a positive refractive power is formed by the fourth lens and the fifth lens,
the sixth lens is cemented to an image sensor, and
the following conditional expressions (1''') and (8) are satisfied:

$$1 \leq (r3f+r3r)/(r3f-r3r) \leq 5 \tag{1'''}$$

$$-1.45 \leq f3/f5 \leq -1 \tag{8}$$

where,
r3f denotes a radius of curvature of an object-side surface of the third lens,
r3r denotes a radius of curvature of an image-side surface of the third lens,
f3 denotes a focal length of the third lens, and
f5 denotes a focal length of the fifth lens.

12. An objective optical system for an endoscope, the objective optical system consisting of, in order from an object side:
a first lens having a negative refractive power,
a second lens having a positive refractive power,
an aperture stop,
a third lens having a positive refractive power,
a fourth lens having a positive refractive power,
a fifth lens having a negative refractive power, and
a sixth lens having a positive refractive power,
wherein:
the second lens is a meniscus lens having a convex surface directed toward an image side,
the third lens is a meniscus lens having a convex surface directed toward the image side,
a cemented lens having a positive refractive power is formed by the fourth lens and the fifth lens,
the sixth lens is cemented to an image sensor, and
the following conditional expressions (1''') and (11) are satisfied:

$$1 \leq (r3f+r3r)/(r3f-r3r) \leq 5 \tag{1'''}$$

$$-15 \leq f45/f1 \leq -3 \tag{11}$$

where,
r3f denotes a radius of curvature of an object-side surface of the third lens,
r3r denotes a radius of curvature of an image-side surface of the third lens,
f45 denotes a focal length of the cemented lens, and
f1 denotes a focal length of the first lens.

* * * * *